US011266346B2

(12) United States Patent
Shin et al.

(10) Patent No.: US 11,266,346 B2
(45) Date of Patent: Mar. 8, 2022

(54) METHOD AND APPARATUS FOR DETERMINING SLEEP STATE USING BIOMETRIC INFORMATION AND MOTION INFORMATION

(71) Applicant: ELECTRONICS AND TELECOMMUNICATIONS RESEARCH INSTITUTE, Daejeon (KR)

(72) Inventors: Hyun Soon Shin, Sejong-si (KR); Do Hyung Kang, Seoul (KR); Chan Young Hahm, Daejeon (KR)

(73) Assignee: ELECTRONICS AND TELECOMMUNICATIONS RESEARCH INSTITUTE, Daejeon (KR)

(*) Notice: Subject to any disclaimer, the term of this patent is extended or adjusted under 35 U.S.C. 154(b) by 242 days.

(21) Appl. No.: 15/997,953

(22) Filed: Jun. 5, 2018

(65) Prior Publication Data

US 2018/0353125 A1 Dec. 13, 2018

(30) Foreign Application Priority Data

Jun. 7, 2017 (KR) .......................... 10-2017-0070972
Feb. 28, 2018 (KR) .......................... 10-2018-0024655

(51) Int. Cl.
*A61B 5/00* (2006.01)
*A61B 5/11* (2006.01)
(52) U.S. Cl.
CPC .......... *A61B 5/4815* (2013.01); *A61B 5/1118* (2013.01); *A61B 5/4812* (2013.01);
(Continued)

(58) Field of Classification Search
CPC ... A61B 5/4815; A61B 5/4812; A61B 5/1118; A61B 5/7264; A61B 5/681; A61B 5/6887; G16H 50/20
See application file for complete search history.

(56) References Cited

U.S. PATENT DOCUMENTS

2009/0121826 A1   5/2009   Song et al.
2010/0286533 A1*  11/2010  Lee .................... A61B 5/0205
                                              600/484
(Continued)

FOREIGN PATENT DOCUMENTS

JP      2017-080154 A     5/2017
KR      10-0942696 B1     2/2010
(Continued)

OTHER PUBLICATIONS

Purves D, Augustine GJ, Fitzpatrick D, et al., editors. Neuroscience. 2nd edition. Sunderland (MA): Sinauer Associates; 2001. Physiological Changes in Sleep States. Available from: https://www.ncbi.nlm.nih.gov/books/NBK10916/ (Year: 2001).*
(Continued)

*Primary Examiner* — Gary Jackson
*Assistant Examiner* — Sebastian X Lukjan
(74) *Attorney, Agent, or Firm* — LRK Patent Law Firm

(57) ABSTRACT

A sleep state determination method using biometric and motion information includes acquiring motion information of a user using a motion sensor; determining a primary sleep state of the user based on the acquired motion information; acquiring biometric information of the user using a biometric sensor when the primary sleep state is determined; and determining a final sleep state of the user by combining the acquired biometric information and the primary sleep state.

13 Claims, 11 Drawing Sheets

(52) U.S. Cl.
CPC ............ *A61B 5/681* (2013.01); *A61B 5/7264* (2013.01); *A61B 5/6887* (2013.01)

(56) References Cited

U.S. PATENT DOCUMENTS

| | | |
|---|---|---|
| 2013/0144182 A1 | 6/2013 | Jeong et al. |
| 2014/0278229 A1* | 9/2014 | Hong ............... A61B 5/486 702/160 |
| 2015/0109124 A1* | 4/2015 | He ............... A61B 5/02055 340/539.12 |
| 2016/0089078 A1* | 3/2016 | Du ............... A61B 5/4812 600/301 |
| 2017/0135629 A1* | 5/2017 | Kent ............... A61B 5/389 |

FOREIGN PATENT DOCUMENTS

| | | | |
|---|---|---|---|
| KR | 10-2012-0033776 A | 4/2012 | |
| KR | 10-1218626 B1 | 1/2013 | |
| KR | 10-2013-0063364 A | 6/2013 | |
| KR | 10-2014-0120513 A | 10/2014 | |
| WO | 2012/156427 A1 | 11/2012 | |
| WO | WO-2016108751 A1 * | 7/2016 | ......... A61B 5/02405 |
| WO | WO-2016151445 A1 * | 9/2016 | ......... G06F 19/3481 |

OTHER PUBLICATIONS

W. S. Kim, "Classifying sleep stages by using heart rate variability", Society for Emotion and Sensibility, 2009.

\* cited by examiner

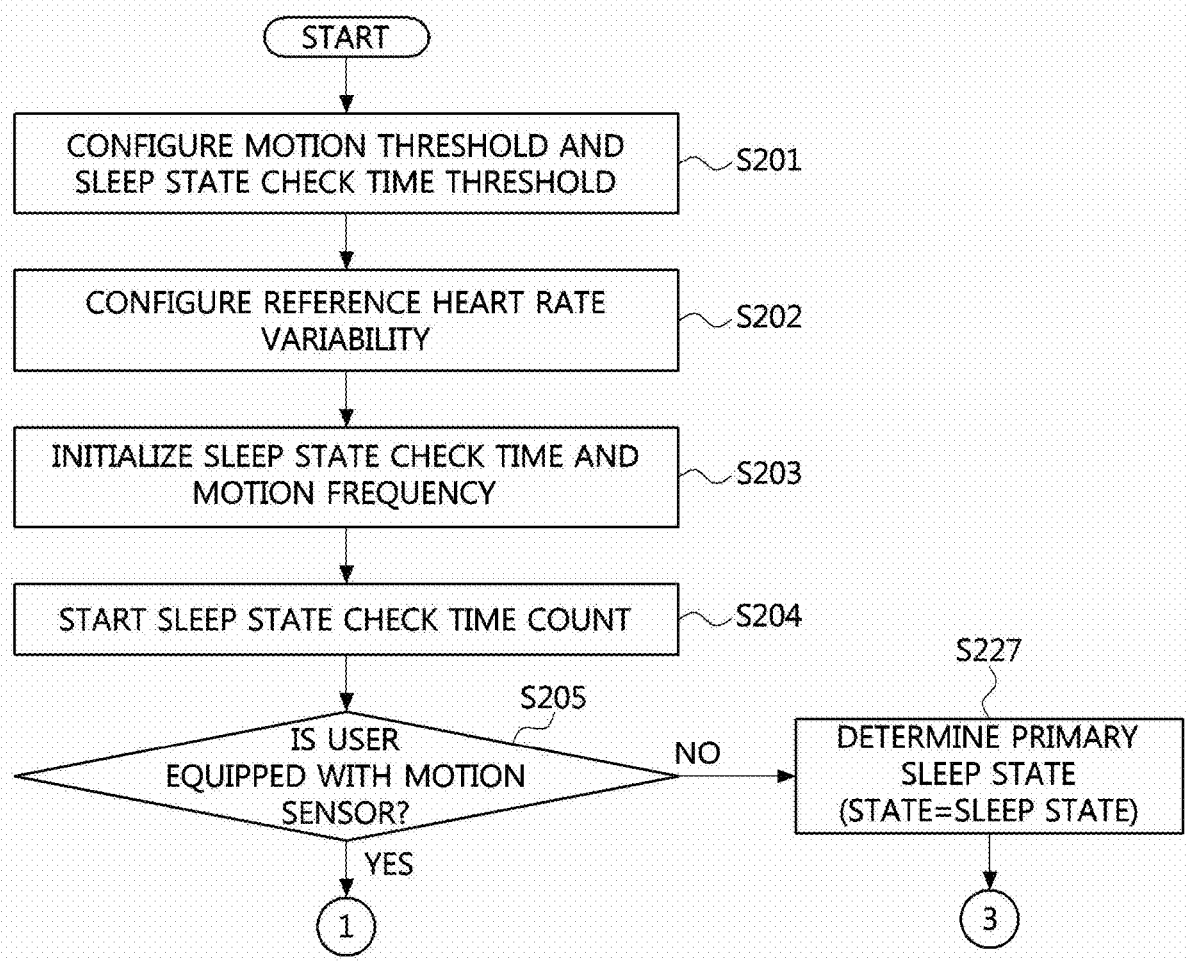

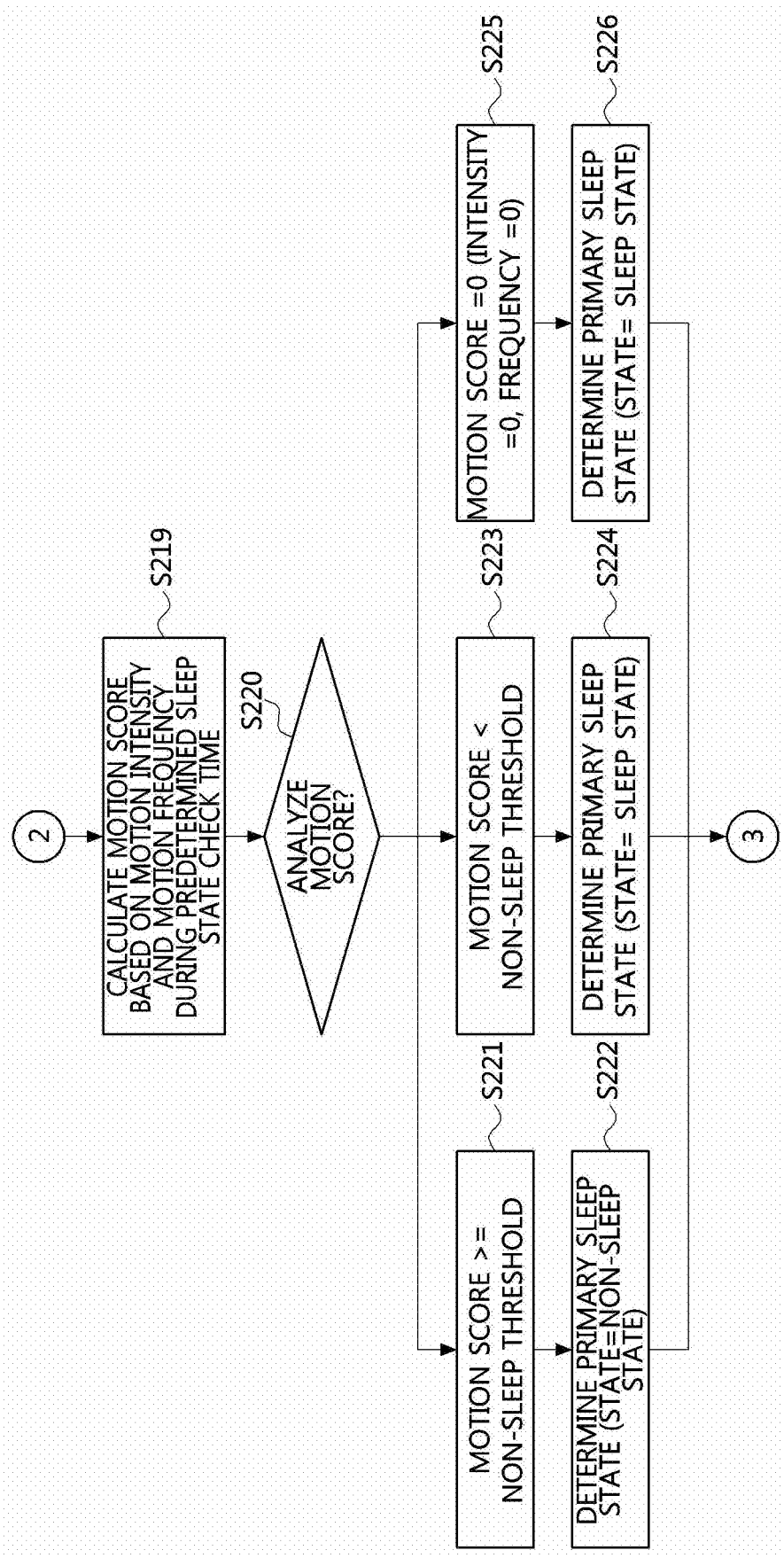

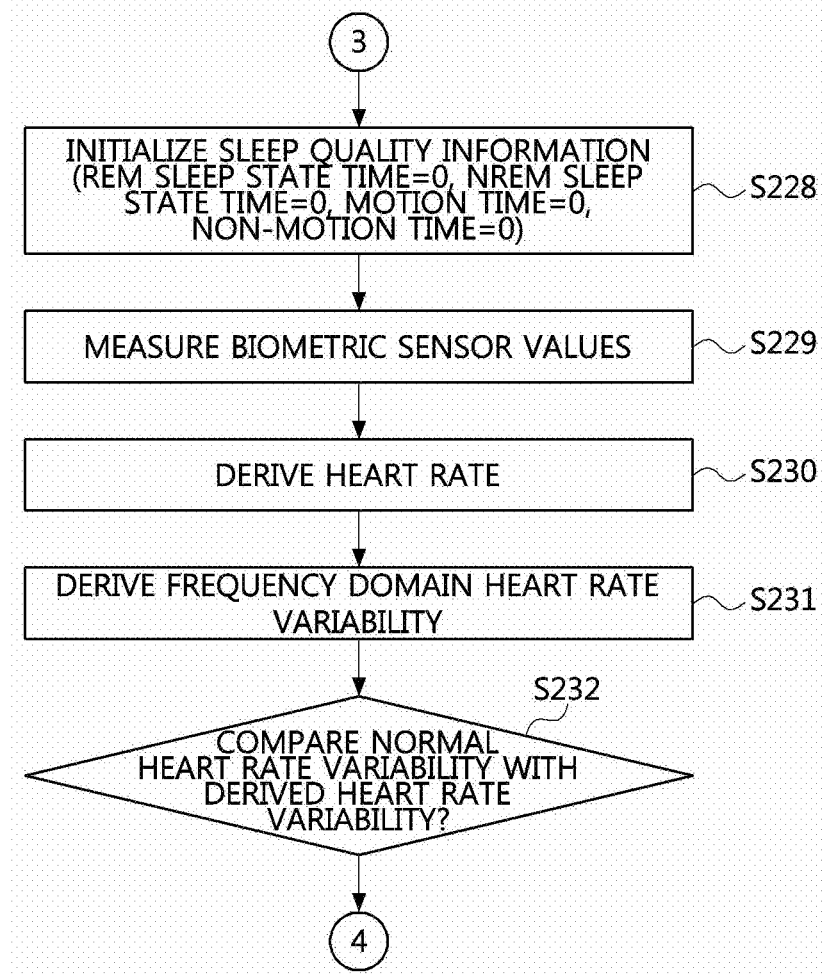

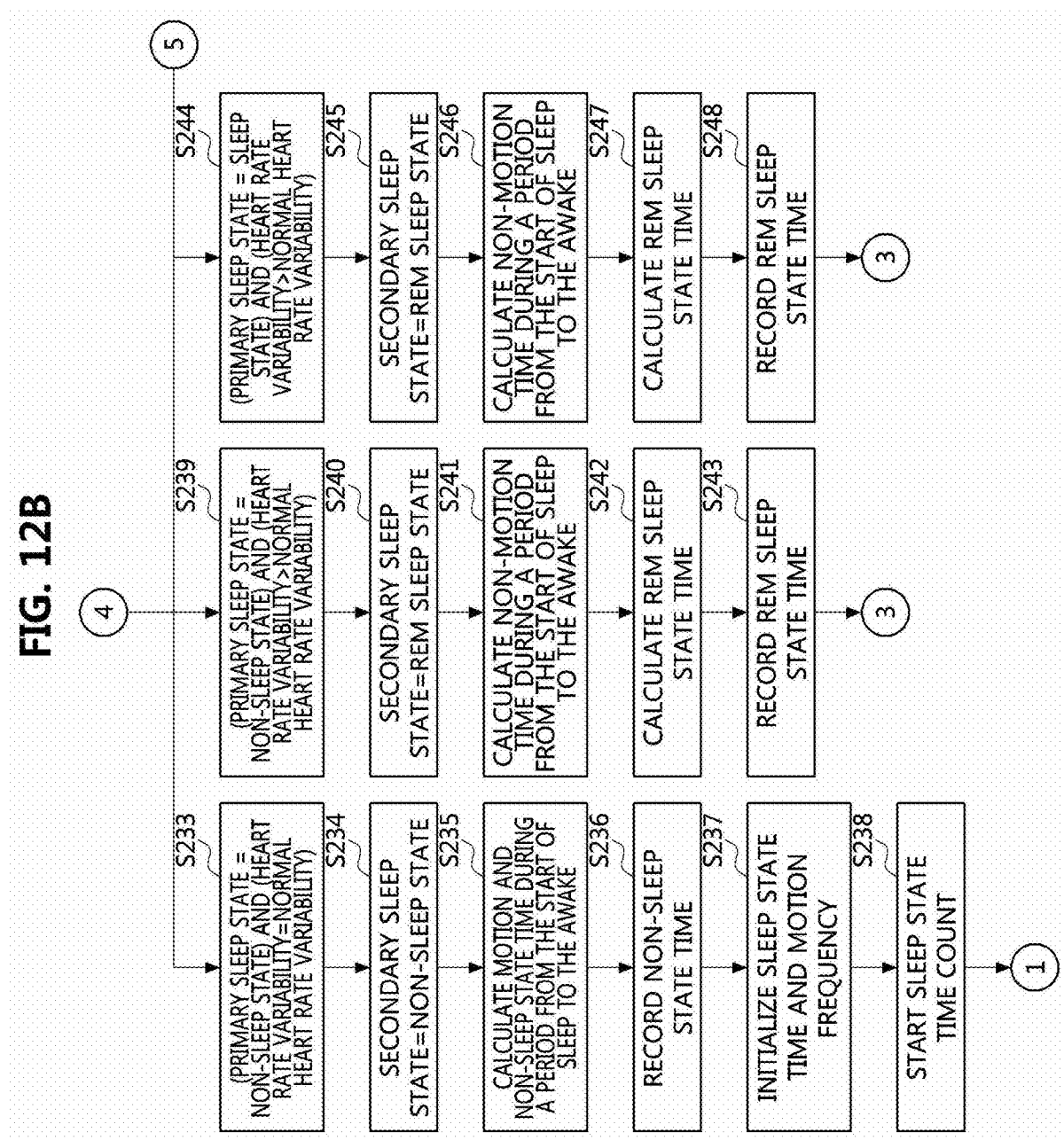

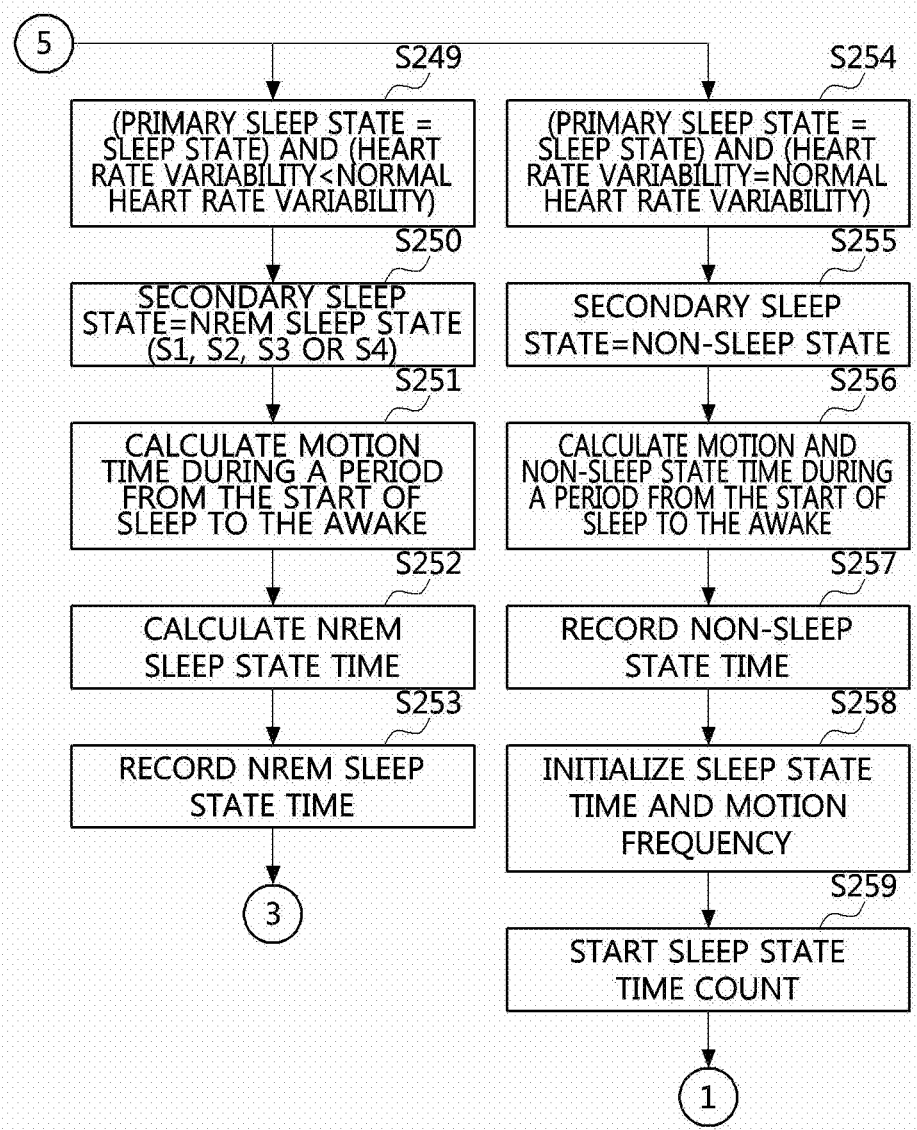

METHOD AND APPARATUS FOR
DETERMINING SLEEP STATE USING
BIOMETRIC INFORMATION AND MOTION
INFORMATION

CROSS-REFERENCE TO RELATED APPLICATIONS

This application claims priority to Korean Patent Applications No. 10-2017-0070972, filed Jun. 7, 2017, and No. 10-2018-0024655, filed Feb. 28, 2018, in the Korean Intellectual Property Office (KIPO), the entire contents of which are hereby incorporated by reference.

BACKGROUND

1. Technical Field

The present disclosure relates to a method and an apparatus for sensing a sleep state using biometric data and motion information, and more specifically, to a method and an apparatus for sensing a precise sensing state by collecting motion information to identify a primary sleep state and collecting biometric data to identify a secondary sleep state.

2. Description of Related Art

Recently, as the importance of sleeping has been emphasized in many reports that healthy sleep is a great help in improving the quality of life, researches are continuously carried out to determine a sleeping state of a user.

According to a sleep management service using devices such as a smart watch, a smart band, a smart phone, and the like among, devices capable of detecting a sleep state, a motion of the user is measured by one or more motion sensors, and a sleep state and a wake states can be classified using the measured signals.

However, since the conventional method using the motion sensor only determines whether the user's sleep state or non-sleep state changes or not, there is a problem that a precise sleep state such as a Rapid Eye Movement (REM) sleep state cannot be determined. Also, since the sleep state is determined based only on the motion sensor that measures the motion of the user, there is a problem that the sleep state is erroneously determined when the user does not move for a long time.

SUMMARY

Accordingly, embodiments of the present disclosure provide a method of determining a sleep state using biometric information and motion information.

Also, embodiments of the present disclosure provide an apparatus of determining a sleep state using biometric information and motion information.

Also, embodiments of the present disclosure provide a method of determining a sleep state using biometric information.

In order to achieve the objective of the present disclosure, a sleep state determination method using biometric and motion information may comprise acquiring motion information of a user using a motion sensor; determining a primary sleep state of the user based on the acquired motion information; acquiring biometric information of the user using a biometric sensor when the primary sleep state is determined; and determining a final sleep state of the user by combining the acquired biometric information and the primary sleep state.

The determining a primary sleep state may comprise calculating a motion intensity and a motion frequency from the motion information; calculating a motion score based on the calculated motion intensity and motion frequency; and determining the primary sleep state of the user based on the calculated motion score.

The motion frequency may be a number of times the motion intensity exceeds a preset threshold during a predetermined time.

In the determining the primary sleep state of the user based on the calculated motion score, the primary sleep state of the user may be determined to be one of a sleep state or a non-sleep state based on the motion score.

The biometric information may include a photoplethysmography (PPG) signal of the user.

The determining a final sleep state may comprise calculating a heart rate variability by analyzing the PPG signal; comparing the calculated heart rate variability with a predetermined normal heart rate variability; and determining the final sleep state by combining a result of the comparison and the primary sleep state.

In the determining the final sleep state, when the calculated heart rate variability is greater than the predetermined normal heart rate variability, the final sleep state may be determined to be a Rapid Eye Movement (REM) sleep state regardless of the primary sleep state.

In the determining the final sleep state, when the calculated heart rate variability is equal to the predetermined normal heart rate variability within a predetermined error range, the final sleep state may be determined to be a non-sleep state regardless of the primary sleep state.

In the determining the final sleep state, when the calculated heart rate variability is smaller than the predetermined normal heart rate variability and the primary sleep state is a sleep state, the final sleep state may be determined to be a non-REM (NREM) sleep state.

In order to achieve the objective of the present disclosure, a sleep state determination apparatus using biometric and motion information may comprise at least one processor and a memory storing at least one instruction executed by the at least one processor. Also, the at least one instruction may be configured to acquire motion information of a user using a motion sensor; determine a primary sleep state of the user based on the acquired motion information; acquire biometric information of the user using a biometric sensor when the primary sleep state is determined; and determine a final sleep state of the user by combining the acquired biometric information and the primary sleep state.

In the determining of the primary sleep state, the at least one instruction may be further configured to calculate a motion intensity and a motion frequency from the motion information; calculate a motion score based on the calculated motion intensity and motion frequency; and determine the primary sleep state of the user based on the calculated motion score.

The motion frequency may be a number of times the motion intensity exceeds a preset threshold during a predetermined time.

In the determining of the primary sleep state, the at least one instruction may be further configured to determine the primary sleep state of the user to be one of a sleep state or a non-sleep state based on the motion score.

The biometric information may include a photoplethysmography (PPG) signal of the user.

In the determining of the final sleep state, the at least one instruction may be further configured to calculate a heart rate variability by analyzing the PPG signal; compare the calculated heart rate variability with a predetermined normal heart rate variability; and determine the final sleep state by combining a result of the comparison and the primary sleep state.

In the determining of the final sleep state, the at least one instruction may be further configured to determine the final sleep state to be a Rapid Eye Movement (REM) sleep state regardless of the primary sleep state when the calculated heart rate variability is greater than the predetermined normal heart rate variability.

In the determining of the final sleep state, the at least one instruction may be further configured to determine the final sleep state to be a non-sleep state regardless of the primary sleep state when the calculated heart rate variability is equal to the predetermined normal heart rate variability within a predetermined error range.

In the determining of the final sleep state, the at least one instruction may be further configured to determine the final sleep state to be a non-REM (NREM) sleep state when the calculated heart rate variability is smaller than the predetermined normal heart rate variability and the primary sleep state is a sleep state.

In order to achieve the objective of the present disclosure, a sleep state determination method using biometric information may comprise acquiring biometric information of a user using a biometric sensor; calculating a heart rate variability by analyzing a photoplethysmography (PPG) signal included in the biometric information; comparing the calculated heart rate variability with a predetermined normal heart rate variance; and determining a sleep state of the user based on a result of the comparison.

The sleep state of the user may be determined to be one of a non-sleep state, a REM sleep state, and a NREM sleep state based on the result of the comparison.

Using the apparatus and method for determining a sleep state based on the biometric and motion information according to the present disclosure as described above, the sleep state can be determined by combining the biometric information and the motion information, so that a more accurate sleep state can be determined.

Also, since information on a sleep cycle according to the determined sleep states is provided to the user, it can be made easy for the user to determine a life pattern according to the information on the sleep cycle. Also, since the sleep state and the sleep quality can be determined by using a biometric sensor in a wearable device having a built-in motion sensor, it can be easily used as a medical assistance device in a home or a medical institution.

BRIEF DESCRIPTION OF DRAWINGS

Embodiments of the present disclosure will become more apparent by describing in detail embodiments of the present disclosure with reference to the accompanying drawings, in which:

FIGS. 11A to 11C are flowcharts illustrating a primary sleep state determination process using motion information in a sleep state determination method using biometric and motion information according to an embodiment of the present disclosure; and FIGS. 12A to 12C are flowcharts illustrating a secondary sleep state determination process using biometric information in a sleep state determination method using biometric and motion information according to an embodiment of the present disclosure.

DETAILED DESCRIPTION

Figure 1:
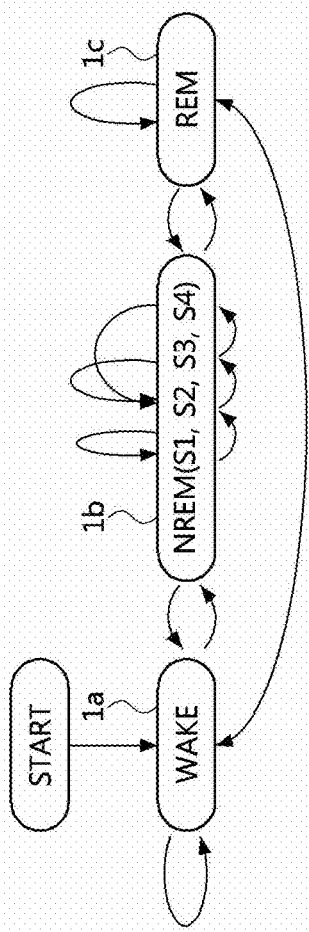
FIG. 1 is a conceptual diagram for explaining a sleep state transition according to an embodiment of the present disclosure.

Embodiments of the present disclosure are disclosed herein. However, specific structural and functional details disclosed herein are merely representative for purposes of describing embodiments of the present disclosure, however, embodiments of the present disclosure may be embodied in many alternate forms and should not be construed as limited to embodiments of the present disclosure set forth herein.

Accordingly, while the present disclosure is susceptible to various modifications and alternative forms, specific embodiments thereof are shown by way of example in the drawings and will herein be described in detail. It should be understood, however, that there is no intent to limit the present disclosure to the particular forms disclosed, but on the contrary, the present disclosure is to cover all modifications, equivalents, and alternatives falling within the spirit and scope of the present disclosure. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (i.e., "between" versus "directly between," "adjacent" versus "directly adjacent," etc.).

The terminology used herein is for the purpose of describing particular embodiments only and is not intended to be limiting of the present disclosure. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this present disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, embodiments of the present disclosure will be described in greater detail with reference to the accompanying drawings.

FIG. 1 is a conceptual diagram for explaining a sleep state transition according to an embodiment of the present disclosure.

Referring to FIG. 1, in the present disclosure, a sleep state of a user may be divided into a non-sleep (i.e., WAKE) state 1a, a Non-Rapid Eye Movement (NREM) sleep state 1b, and a Rapid Eye Movement (REM) sleep state 1c. Here, the NREM sleep state 1b may be subdivided into at least one detailed step (e.g., S1, S2, S3 and S4) according to a degree and a depth of the sleep.

According to an embodiment of the present disclosure, it may be possible to determine whether to transition from each state to another state, rather than just determining the WAKE state 1a, the NREM sleep state 1b, or the REM sleep state 1c. Here, the transition of the sleep state may be determined whether a transition occurs by one step according to the state transition relationship between the WAKE state 1a, the NREM sleep state 1b and the REM sleep state 1c, or whether a transition occurs by two or more steps (e.g., a transition from the WAKE state 1a to the REM sleep state 1c, or a transition from the S4 of the NREM sleep state 1b to the S2 of the NREM sleep state 1b).

Also, according to an embodiment of the present disclosure, it may be also possible to determine a transition to the same state (i.e., maintaining the same state) such as a transition from the WAKE state 1a to the WAKE state 1a or a transition from the REM sleep state 1c to the REM sleep state 1c.

Figure 2:
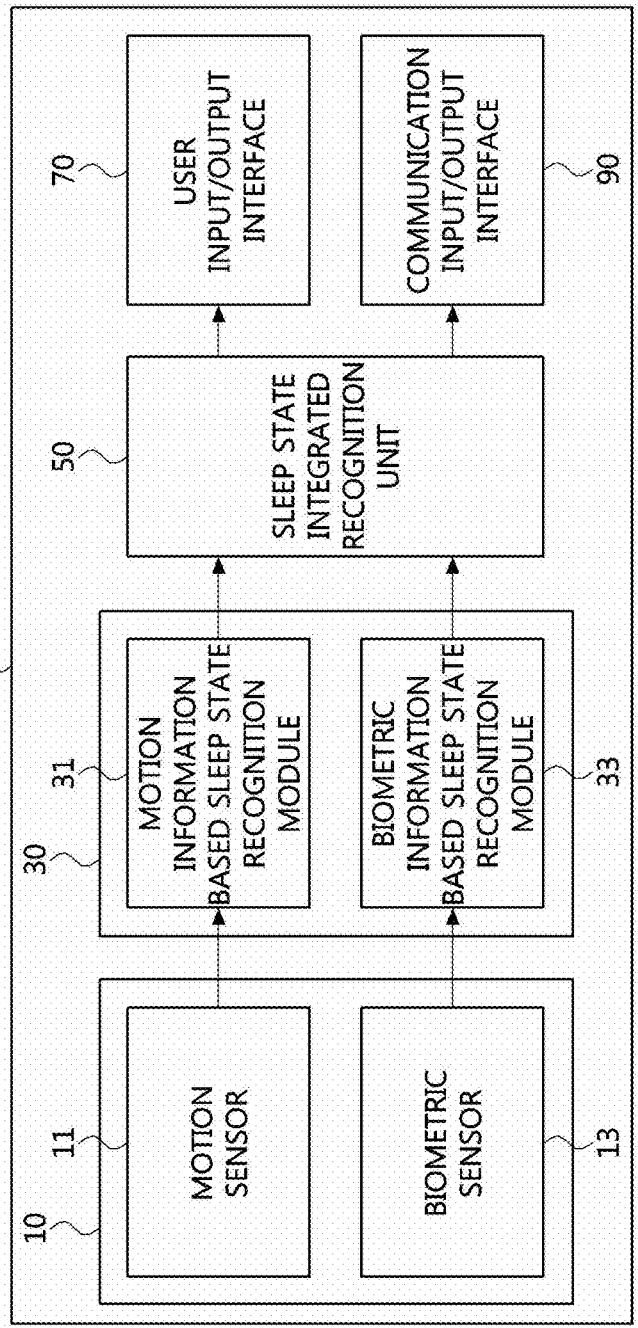
FIG. 2 is a block diagram illustrating a sleep state determination apparatus using biometric and motion information according to an embodiment of the present disclosure.

FIG. 2 is a block diagram illustrating a sleep state determination apparatus using biometric and motion information according to an embodiment of the present disclosure.

Referring to FIG. 2, a sleep state determination apparatus 100 using biometric and motion information according to an embodiment of the present disclosure may comprise a sensor unit 10, a sleep state recognition unit 30, a sleep state integrated recognition unit 50, a user input/output interface 70, and a communication input/output interface 90.

The sensor unit 10 may include a motion sensor 11 and a biometric sensor 13. Here, the sensor unit 10 may be embodied in a wearable device such as a smart band, a smart watch, a smart clothing, or the like. Alternatively, the sleep state determination apparatus 100 may be implemented as the wearable device. Therefore, the motion sensor 11 and the biometric sensor 13 may be worn on the user's wrist or the like.

The motion sensor 11 may include, but is not limited to, a geomagnetic sensor, a gyroscope sensor, a gravity sensor, and the like, which can detect a motion of the user. The biometric sensor 13 may be a photoplethysmograph (PPG) sensor for measuring a blood flow of the user's body through optical characteristics to estimate a heart activity of the user, but the present disclosure is not limited thereto. The motion sensor 11 and the biometric sensor 13 may be worn on the user's wrist to measure data.

The sleep state recognition unit 30 may include a motion information based sleep state recognition module 31 and a biometric information based sleep state recognition module 33. The motion information based sleep state recognition module 31 may recognize a sleep state based on the motion information acquired by the motion sensor 11, and the biometric information based sleep state recognition module 33 may recognize a sleep state based on the biometric information acquired by the biometric sensor 13.

The sleep state integrated recognition unit 50 may analyze and manage a sleep quality by combining the results of two modules 31 and 33 in the sleep state recognition unit 30. According to an embodiment of the present disclosure, the sleep state integrated recognition unit 50 may detect a sleep and wake cycle and a REM and NREM sleep cycle based on information on the sleep states or the non-sleep state obtained from the motion information based sleep state recognition module 31 and information on the REM sleep state or the NREM sleep state obtained from the biometric information based sleep state recognition module 33. That is, the sleep state integrated recognition unit 50 may analyze data based on the results of the sleep state recognition unit 30 to determine a final sleep state and determine a quality of the sleep state.

The user input/output interface 70 may include a display device, a vibration device, and the like to output the results of the sleep state recognition unit 30 and the sleep state integrated recognition unit 50 so that the results can be recognized s and tactually by the user. Also, the user input/output interface 70 may include a touch screen, a keyboard, a mouse, and the like for receiving inputs such as users initial settings, operation commands, and the like.

The communication input/output interface 90 may be a wired or wireless communication network module for transmitting the results of the sleep state recognition unit 30 and the sleep state integrated recognition unit 50 to an external server, a database, or the like.

Figure 3:
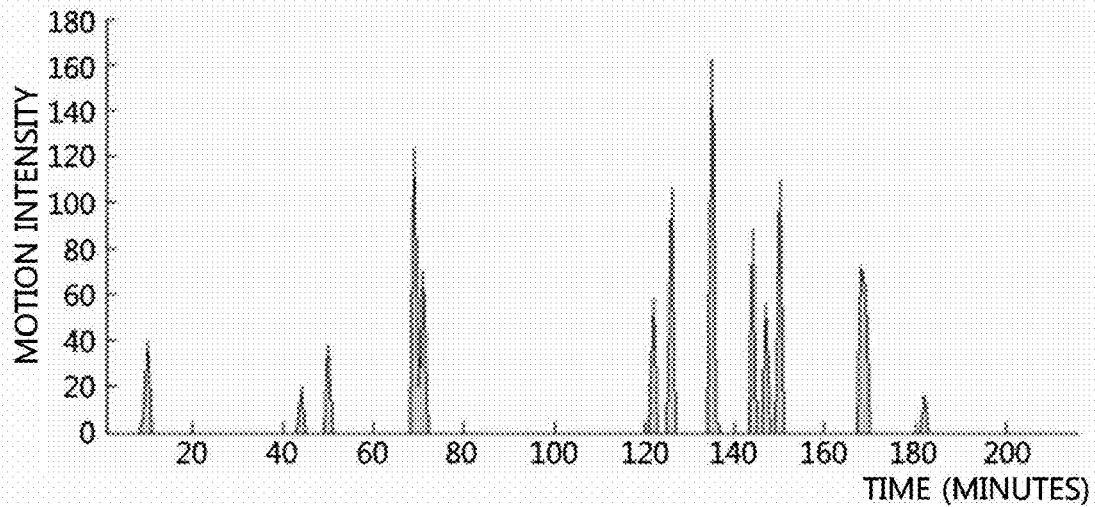
FIG. 3 is a graph illustrating only values equal to or greater than a threshold among motion data measured by a motion sensor.

FIG. 3 is a graph illustrating only values equal to or greater than a threshold among motion data measured by a motion sensor.

Motions of the user may be sensed through the motion sensor 11, and the sensed motions (e.g., band-pass filtered 16 Hz raw data) may be analyzed. FIG. 3 illustrates only motion intensities equal to or greater than a threshold. Here, the horizontal axis represents the time at which the motions are sensed, and the vertical axis represents the motion intensities.

Here, the motion intensity (e.g., a motion value (MV)) is a value obtained by calculating a motion magnitude based on the motion information of the user. When the motion information includes a motion displacement of the user in the x, y, and z directions, the motion intensity may be represented as Equation 1 below.

$$MV=\sqrt{x^2+y^3+z^2} \quad \text{[Equation 1]}$$

Referring to Equation 1, in the present disclosure, the motion intensity may mean a motion displacement of the user (or wearable device worn by a user).

Figure 4:
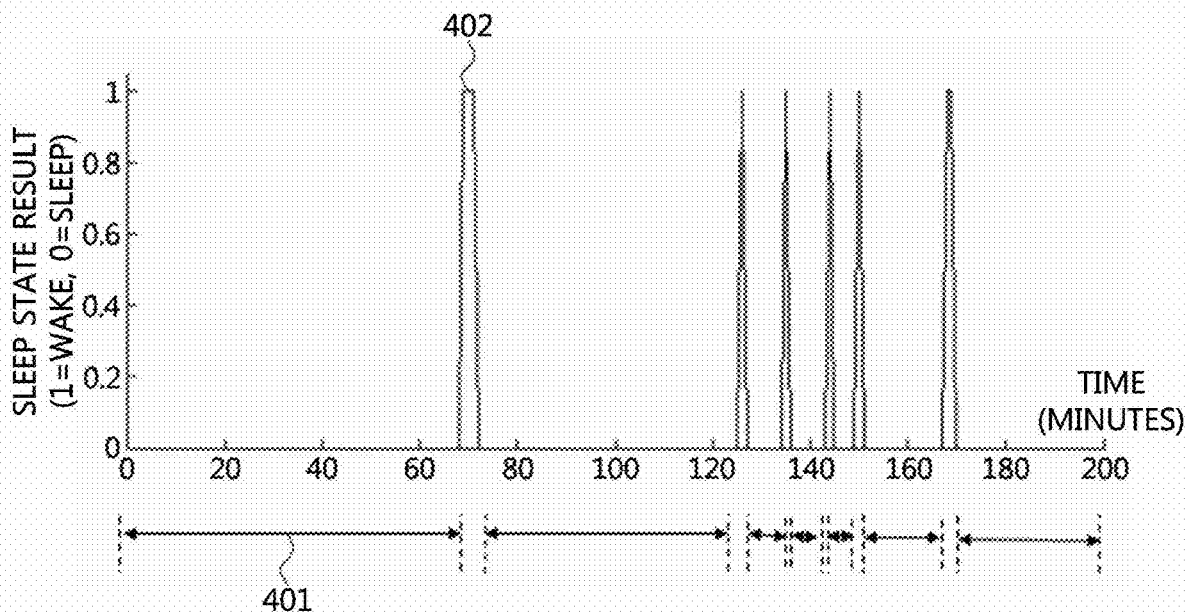
FIG. 4 is a graph illustrating a result of determining a sleep state using motion information.

FIG. 4 is a graph illustrating a result of determining a sleep state using motion information.

In an embodiment of the present disclosure, the motion information sensed by the motion sensor may be analyzed to acquire the motion intensities equal to or greater than the threshold as shown in FIG. 3, and the sleep state may be determined by further considering a motion frequency. Here, the motion frequency $Count_{act}$ may be calculated as Equation 2 below.

$$Count_{act} = \begin{cases} 0, & \text{if } MV_n < \text{threshold} \\ \text{otherwise}, & Count_{act}++ \end{cases} \quad \text{[Equation 2]}$$

Referring to Equation 2, it may be determined whether each calculated motion intensity (i.e., $MV_n$) exceeds a threshold. If the corresponding motion intensity $MV_n$ exceeds the threshold, the motion frequency may be increased by one. In this manner, the motion frequency during a predetermined time (or referred to as a sleep state check time) may be calculated.

The sleep state of the user may be determined using an algorithm that comprehensively considers the calculated motion frequency and the motion intensity according to FIG. 3. For example, if the motion frequency calculated during the predetermined time is greater than a threshold, the user may be determined to be in the non-sleep state. Alternatively, if a motion intensity exceeding a second threshold larger than the threshold of Equation 2 exists among the motion intensities calculated for the predetermined time, the user may be determined to be in the non-sleep state. Alternatively, a motion score may be calculated by weighting the calculated motion intensity and the calculated motion frequency, and the sleep state of the user may be determined through the calculated motion score.

Referring to FIG. 4, a sleep state 401 and a non-sleep state 402 may be identified as the result of determining the sleep state based on the motion information.

Figure 5:
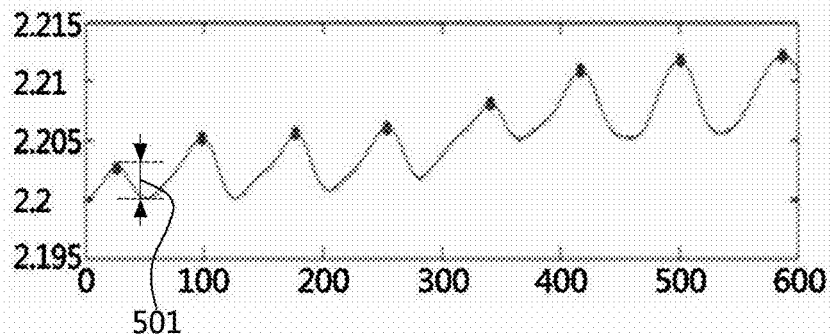
FIG. 5 is a graph illustrating showing a PPG signal measured using a PPG sensor for measuring biometric information.
Figure 6:
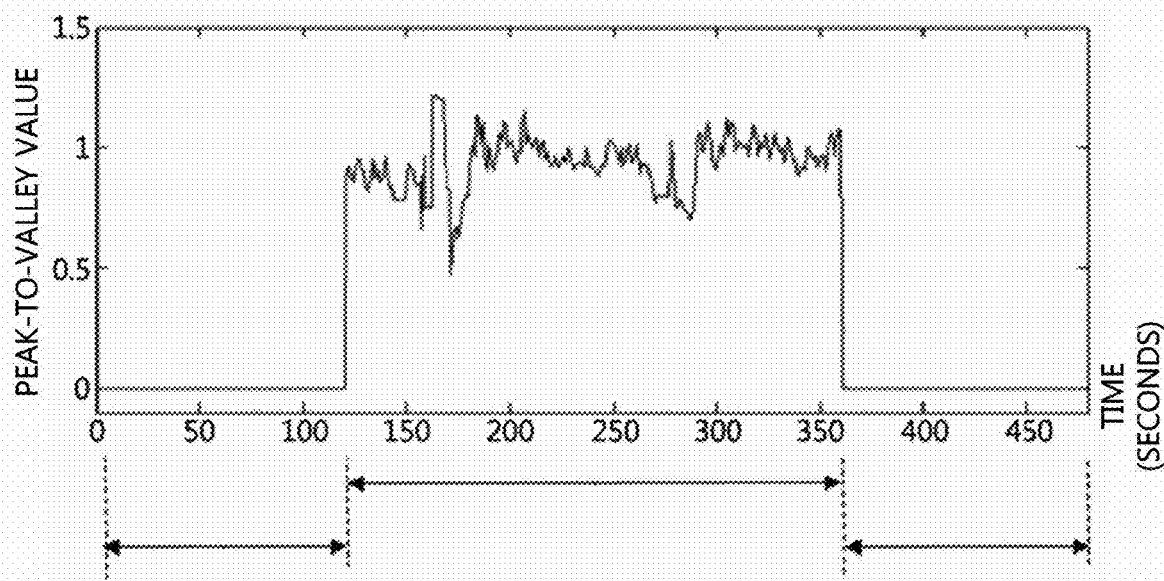
FIG. 6 is a graph illustrating a heart rate extracted using the PPG signal according to FIG. 5.

FIG. 5 is a graph illustrating showing a PPG signal measured using a PPG sensor for measuring biometric information, and FIG. 6 is a graph illustrating a heart rate extracted using the PPG signal according to FIG. 5.

According to an embodiment of the present disclosure, when a PPG sensor is used as the biometric sensor, a PPG signal may be measured. In this case, the measured PPG signal may be as shown in FIG. 5. In FIG. 5, the horizontal axis represents the time axis and the vertical axis represents the amplitude of the PPG signal.

Referring to FIG. 5, a PPG signal with respect to time may be identified. When peak-to-valley values (e.g., 501) of the graph of FIG. 5 are measured and drawn again, a graph may be derived as having peak-to-valley values in the vertical axis. Here, if a frequency is measured (e.g., converted to beats per minute) in the graph of FIG. 6, the user's heart rate 501 may be measured.

Meanwhile, since the process of measuring the biometric information using the biometric sensor is started after determining the sleep state using the motion information in FIG. 4, so that the sleep state determination based on the biometric information may be a secondary sleep state determination after the primary sleep state determination based on the motion information.

Figure 7:
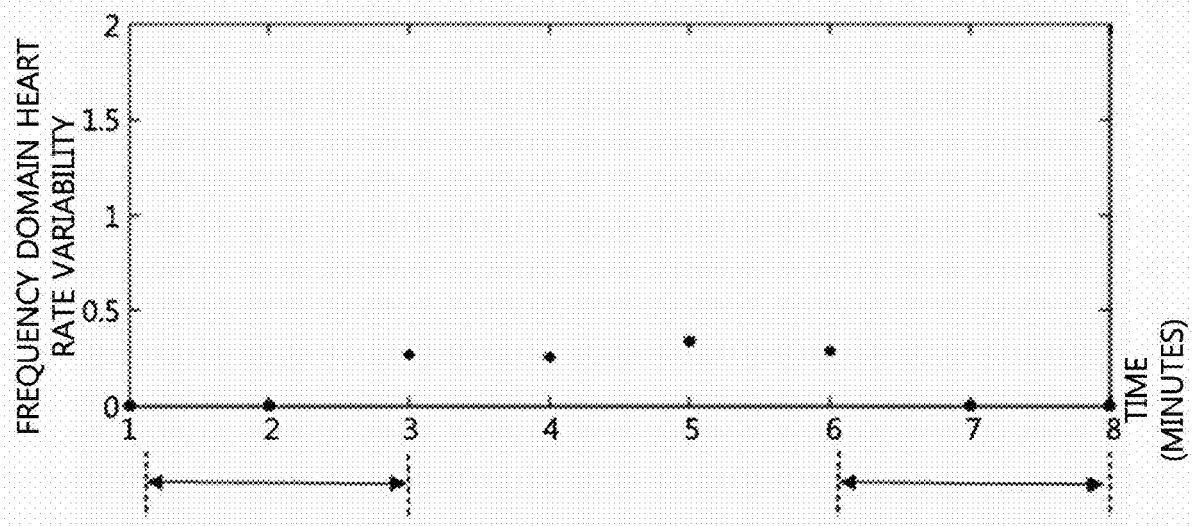
FIG. 7 is a graph illustrating a heart rate variability obtained by analyzing the heart rate according to FIG. 6 in the frequency domain.
Figure 8:
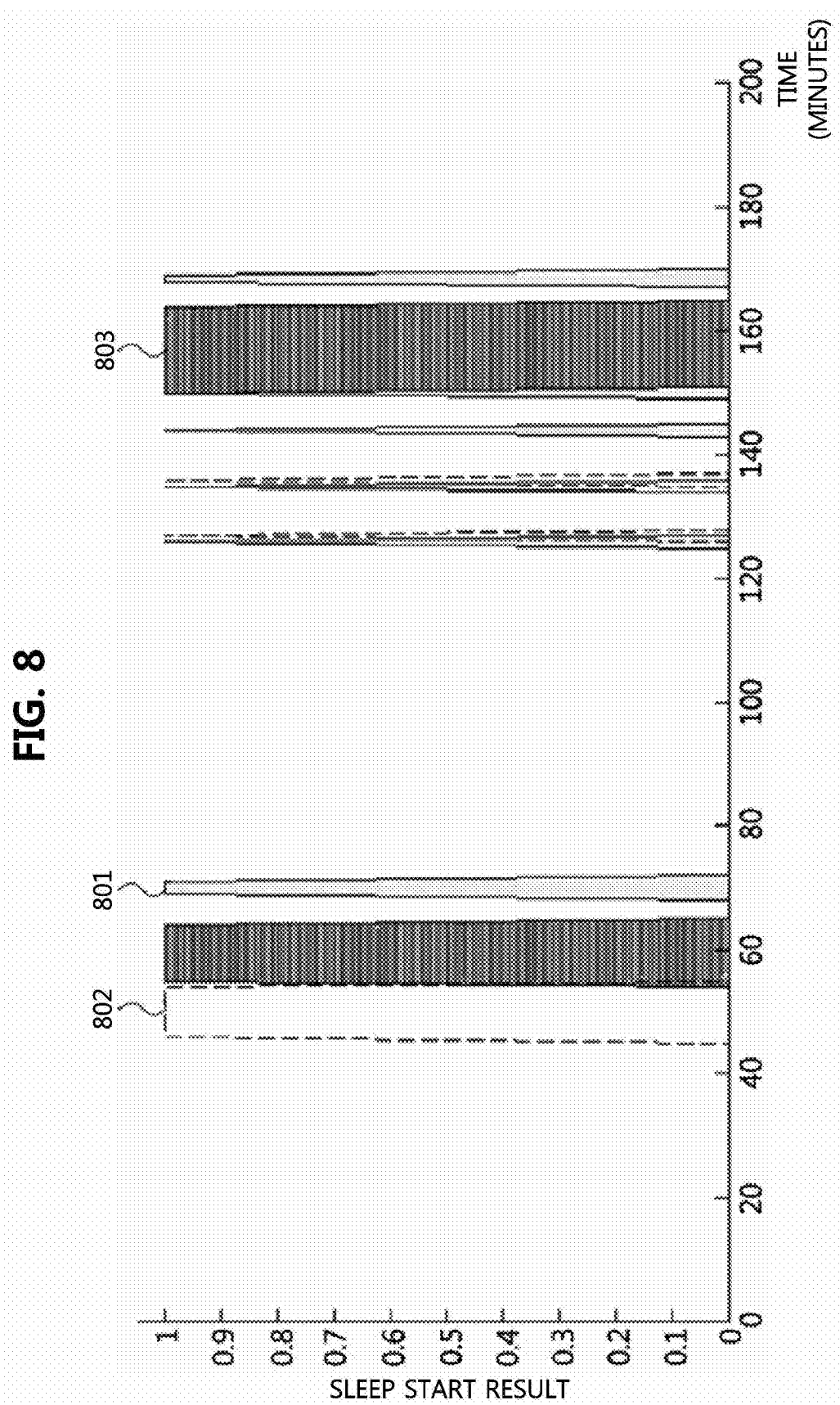
FIG. 8 is a graph illustrating a sleep state determination result using an apparatus and a method of determining a sleep state using biometric and motion information according to an embodiment of the present disclosure.

FIG. 7 is a graph illustrating a heart rate variability obtained by analyzing the heart rate according to FIG. 6 in the frequency domain, and FIG. 8 is a graph illustrating a sleep state determination result using an apparatus and a method of determining a sleep state using biometric and motion information according to an embodiment of the present disclosure.

Referring to FIG. 7, a graph illustrating values derived using the heart rate derived using the peak-to-valley values in FIG. 6 may be identified. Based on the heart rate variability, the user's sleep state may be classified into the REM sleep state, the NREM sleep state, or the non-sleep state, and the result of the classified sleep states of the user may be derived as illustrated in FIG. 8.

Referring to FIG. 8, a non-sleep state 802, a NREM sleep state 801, and a REM sleep state 803 may be identified as the sleep state result over time. According to the sleep state determination method and apparatus using biometric and motion information according to an embodiment of the present disclosure, the sleep quality can be analyzed and the user can be managed based on the sleep state derived as shown in FIG. 8.

Figure 9:
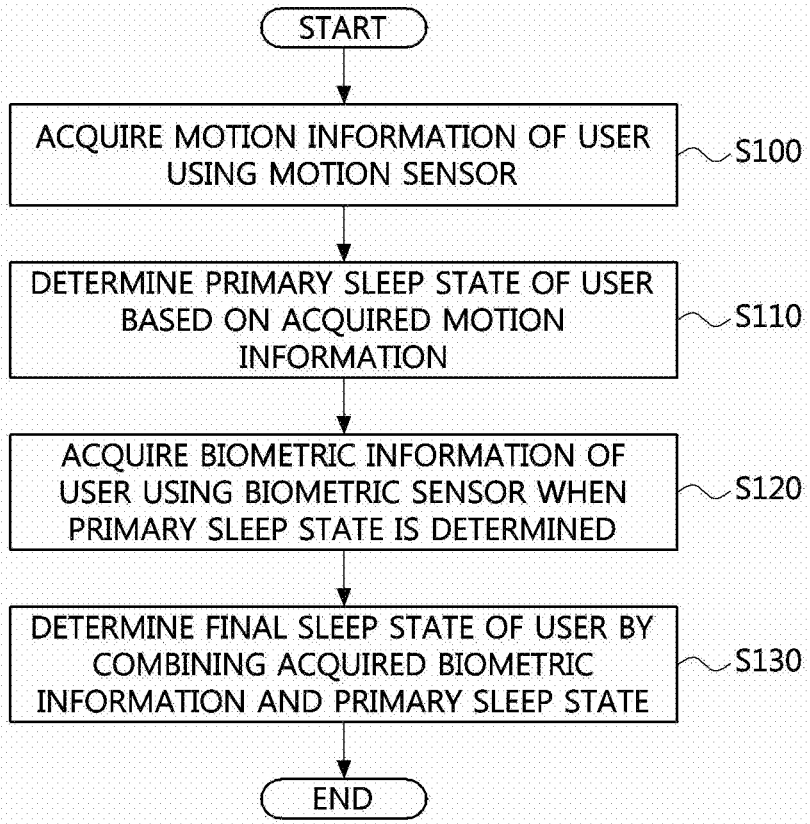
FIG. 9 is a flowchart illustrating a sleep state determination method using biometric and motion information according to an embodiment of the present disclosure.

FIG. 9 is a flowchart illustrating a sleep state determination method using biometric and motion information according to an embodiment of the present disclosure.

Referring to FIG. 9, a sleep state determination method using biometric and motion information may comprise a step S100 of acquiring motion information of a user using a motion sensor, a step S110 of determining a primary sleep state of the user based on the acquired motion information, a step S120 of acquiring biometric information of the user using a biometric sensor when the primary sleep state is determined, and a step S130 of determining a final sleep state of the user by combining the acquired biometric information and the primary sleep state.

Here, the step S110 may comprise calculating a motion intensity and a motion frequency from the motion information, calculating a motion score based on the calculated motion intensity and motion frequency, and determining the primary sleep state of the user based on the motion score.

Here, the motion frequency may be the number of times the motion intensity exceeds a predetermined threshold during a predetermined time (i.e., sleep state check time).

Here, in the determining the primary sleep state of the user based on the motion score, the primary sleep state of the user may be determined to be a sleep state or a non-sleep state.

Here, the biometric information may include a PPG signal for the user.

Here, the step S130 may comprise calculating a heart rate variability by analyzing the PPG signal, comparing the calculated heart rate variability with a predetermined normal heart rate variability, and determining the final sleep state by combining the primary sleep state and the comparison result. Here, daily heart rate variability may be collected in advance and used as the predetermined normal heart rate variability of the user.

In the determining of the final sleep state, the final sleep state may be determined to be the REM sleep state regardless of the primary sleep state, when the calculated heart rate variability is greater than the normal heart rate variability.

In the determining of the final sleep state, the final sleep state may be determined to be the non-sleep state regardless of the primary sleep state, when the calculated heart rate variability is equal to the normal heart rate variability within a predetermined error range.

In the determining of the final sleep state, the final sleep state may be determined to be the NREM sleep state when the primary sleep state is the sleep state and the calculated heart beat variability is less than the normal heart rate variability.

Here, the NREM sleep state may be subdivided into at least two NREM sleep states such as S1, S2, S3 and S4 according to the calculated heart rate variability.

Meanwhile, the sleep state determination method using biometric and motion information may also be implemented using only the biometric information excluding the motion information.

Accordingly, a sleep state determination method using biometric information according to an embodiment of the present disclosure may comprise acquiring biometric information of the user using a biometric sensor, analyzing a PPG signal included in the biometric information to derive a hear rate variability, comparing the calculated heart rate variability with the predetermined normal heart rate variability, and determining a sleep state of the user based on the comparison result.

Here, in the determining of the sleep state of the user, the sleep state of the user may be determined to be one of the WAKE state, the NREM sleep state, and the REM sleep state based on the comparison result.

Here, the sleep state determination method using biometric information should be understood to include the components of the above-described sleep state determination method using biometric information and motion information as well as the above-described steps.

Figure 10:
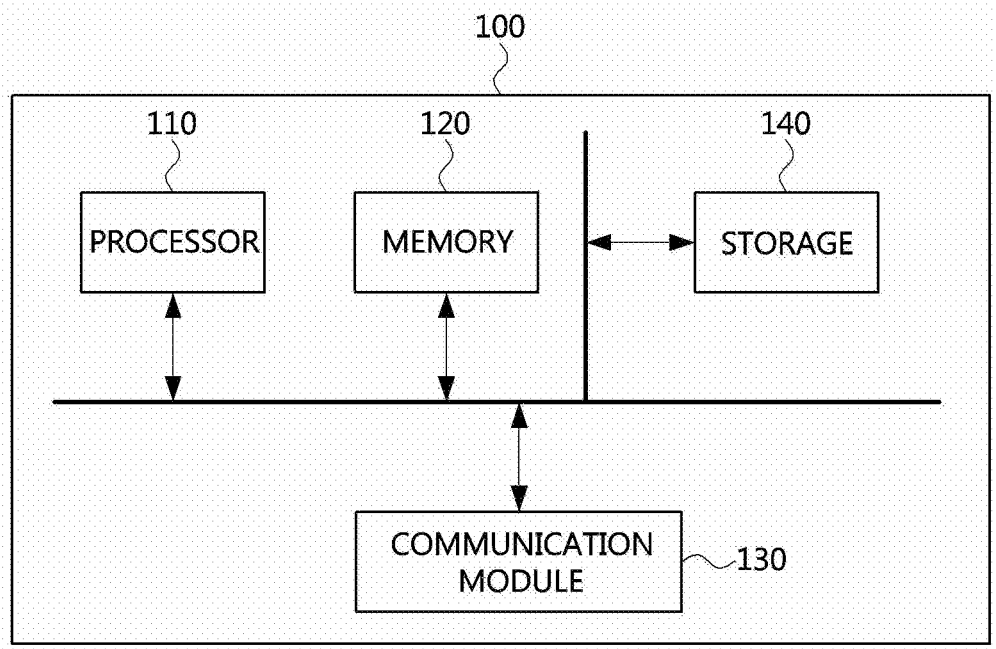
FIG. 10 is a block diagram illustrating a sleep state determination apparatus using biometric and motion information according to an embodiment of the present disclosure.

FIG. 10 is a block diagram illustrating a sleep state determination apparatus using biometric and motion information according to an embodiment of the present disclosure.

Referring to FIG. 10, a sleep state determination apparatus 100 using biometric and motion information may comprise at least one processor 110, and instructions for commanding the at least one processor 110 to perform at least one step, and a memory 120 for storing the instructions.

Here, the sleep state determination apparatus 100 using biometric and motion information may further comprise a communication module 130 for transmitting information on the determined sleep state to an external server or a database and receiving an initial setting command or the like by using a wired or wireless network.

Here, the sleep state determination apparatus 100 using biometric and motion information may further comprise a storage 140 for storing the motion information or the biometric information received from the motion sensor or the biometric sensor, the sleep state determination result, and various setting information.

Here, the at least one step may comprise acquiring the motion information of the user using the motion sensor, determining the primary sleep state of the user based on the acquired motion information, acquiring the biometric information of the user using the biometric sensor when the primary sleep state is determined, and determining the final sleep state of the user by combining the acquired biometric information and the primary sleep state.

Here, the determining of the primary sleep state may comprise calculating the motion intensity and the motion frequency from the motion information, calculating the motion score based on the calculated motion intensity and motion frequency, and determining the primary sleep state of the user based on the motion score.

Here, the motion frequency may be the number of times the motion intensity exceeds a predetermined threshold during a predetermined time (e.g., sleep state check time).

Here, in the determining the primary sleep state of the user based on the motion score, the primary sleep state of the user may be determined as a sleep state or a WAKE (non-sleep) state.

Here, the biometric information may include a PPG signal for the user.

Here, the determining of the final sleep state of the user may comprise calculating a heart rate variability by analyzing the PPG signal, comparing the calculated heart rate variability with the predetermined normal heart rate variability, and determining the final sleep state by combining the primary sleep state and the comparison result.

In the determining of the final sleep state, the final sleep state may be determined to be the REM sleep state regardless of the primary sleep state, when the calculated heart rate variability is greater than the normal heart rate variability.

In the determining of the final sleep state, the final sleep state may be determined to be the non-sleep state regardless of the primary sleep state, when the calculated heart rate variability is equal to the normal heart rate variability within a predetermined error range.

In the determining of the final sleep state, the final sleep state may be determined to be the NREM sleep state when the primary sleep state is the sleep state and the calculated heart beat variability is less than the normal heart rate variability.

Here, the NREM sleep state may be subdivided into at least two NREM sleep states such as S1, S2, S3 and S4 according to the calculated heart rate variability.

Examples of the sleep state determination apparatus 100 may include a desktop computer, a laptop computer, a notebook, a smart phone, a tablet PC, a mobile phone, a smart watch, a smart glass, an e-book reader, a portable multimedia player (PMP), a portable game machine, a navigation device, a digital camera, a digital multimedia broadcasting (DMB) player, a digital audio recorder, a digital audio player, a digital video recorder, a digital video player, a PDA (Personal Digital Assistant), and the like, which includes a communicatable central processing unit (CPU), a memory, and software.

Figure 11B:
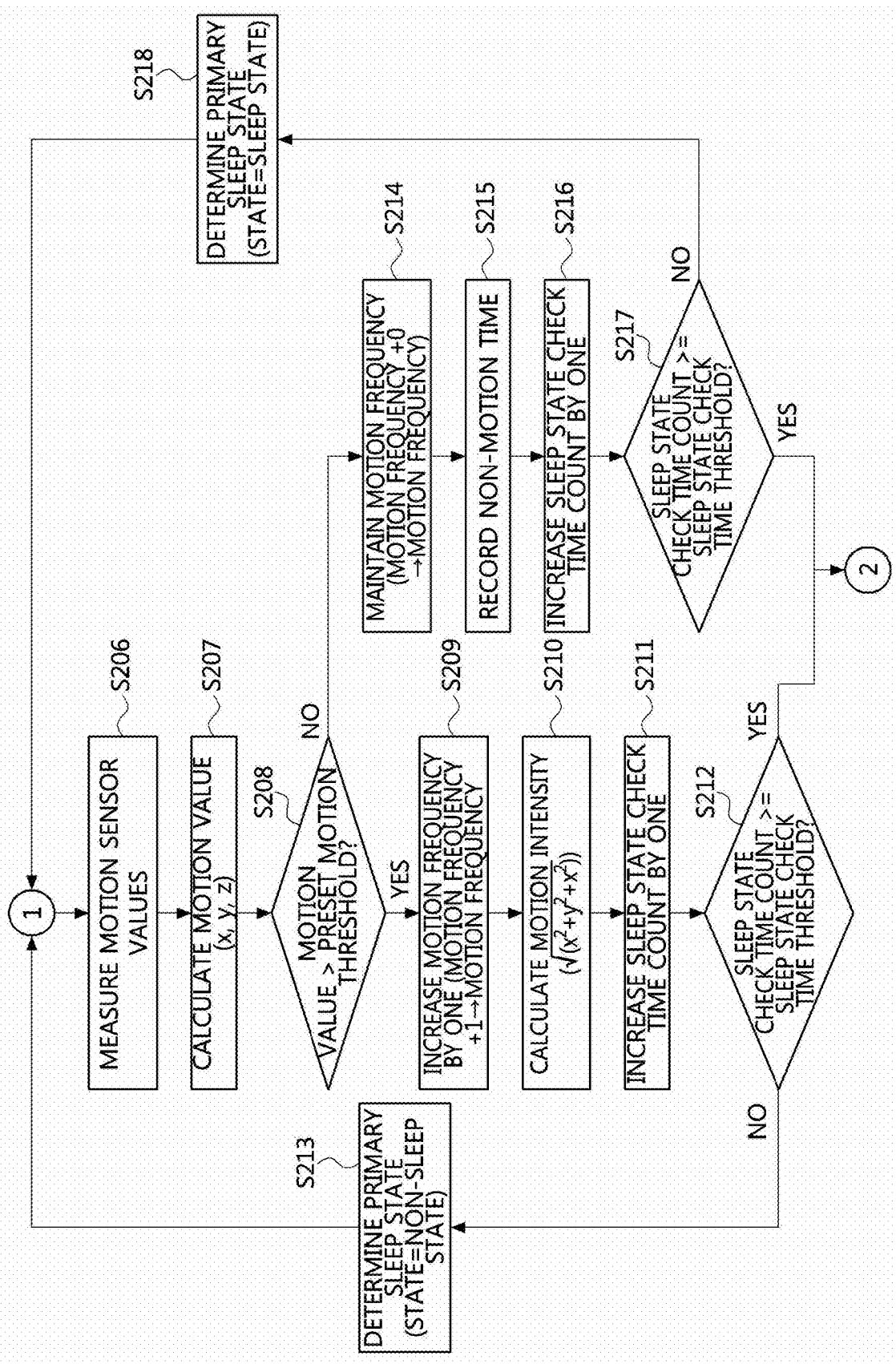

FIGS. 11A to 11C are flowcharts illustrating a primary sleep state determination process using motion information in a sleep state determination method using biometric and motion information according to an embodiment of the present disclosure, and FIGS. 12A to 12C are flowcharts illustrating a secondary sleep state determination process using biometric information in a sleep state determination method using biometric and motion information according to an embodiment of the present disclosure.

Referring to FIG. 11A, a motion threshold and a sleep state check time threshold may be configured (S201), a reference heart rate variability (i.e., a normal heart rate variability or a value obtained by multiplying the normal heart rate variability with an arbitrary variable) may be configured (S202), a sleep state check time may be initialized (e.g., initialized to 0) and/or a motion frequency may be initialized (e.g., initialized to 0) (S203), and a counting for the sleep state check time may be started (S204). Here, the steps S201 to S203 may be performed simultaneously or in a different order regardless of the above-described order.

After performing the steps S201 to S204, it may be checked whether or not a wearable device worn by the user is equipped with a motion sensor module (S205).

Here, the step S205 may be performed by checking whether a signal is received from the motion sensor. Here, in the case of a wearable device to which the motion sensor module is not attached, the primary sleep state may be determined to be the sleep state (S227). After performing the step S227, the determination of the primary sleep state as the sleep state only because the motion score value is '0' (i.e., when the motion intensity and the motion frequency value is '0') may be inadequate because the case that the user is awake without any motion may exist. Therefore, in order to perform the sleep state determination using the biometric information, the information on the sleep quality may be initialized (i.e., REM sleep state time=0, NREM sleep state time=0, motion time=0, non-motion time=0), and the biometric information based sleep state determination may be started (S228).

Meanwhile, in the case of the wearable device equipped with the motion sensor module, the motion sensor signals may be measured using the wearable device according to FIG. 11B (S206), and a motion value may be calculated (S207).

After performing the steps S206 to S207, it may be checked whether the calculated motion value is greater than a preset motion threshold (S208).

When it is determined in the step S208 that the motion intensity is greater than or equal to the preset motion threshold, the motion frequency may be increased by one (S209), a motion intensity may be calculated (S210), and the sleep state check time count may be increased by one (S211). After performing the steps S209 to S211, it may be checked whether the sleep state check time count is greater than or equal to the sleep state check time threshold (S212).

When it is determined in the step S212 that the sleep state check time count is smaller than the sleep state check time threshold, it may be determined that the primary sleep state is the non-sleep state (S213), and the steps S206 to S212 may be repeated to perform the motion information based sleep state determination.

Also, when it is determined in the step S208 that the motion value is smaller than the preset motion threshold, the motion frequency may be maintained as unchanged (S214), the non-motion time may be recorded (S215), and the sleep state check time count may be increased by one (S216). After performing the steps S214 to S216, it may be checked whether the sleep state check time count value is greater than or equal to the sleep state check time threshold (S217). If it is determined in the step S217 that the sleep state check time count is smaller than the sleep state check time threshold, it may be determined that the primary sleep state is the sleep state (S218), and the steps S206 to S217 may be repeated to determine to perform the motion information based sleep state determination.

Here, when the sleep state check time count is equal to or greater than the sleep state check time threshold according to the result of the step S212 or S217, a motion score may be calculated through scoring sleep or non-sleep state based on the motion intensity and motion frequency during the predetermined sleep state check time (S219), and the calculated motion score may be analyzed (S220).

When it is determined in the step S220 that the motion score is equal to or greater than a non-sleep threshold (S221), the primary sleep state may be determined to be the non-sleep state (S222).

When it is determined in the step S220 that the motion score is smaller than the non-sleep threshold (S223), the primary sleep state may be determined to be the sleep state (S224).

When it is determined in the step S220 that the motion score is 0, that is, if there is no motion at all (S225), the primary sleep state may be determined to be the sleep state (S226).

After performing the step S222, it may be inadequate to determine the sleep state as the non-sleep state only because there is a motion. Therefore, in order to accurately determine the sleep state, the sleep quality information may be initialized (i.e., REM sleep state time=0, NREM sleep state time=0, motion time=0, non-motion time=0), and the biometric information based sleep state determination according to FIG. 12A may be started (S227).

Also, after performing the step S224 or S226, since the user's motion may be limited or small while the user is awake, it may be inadequate to determine the sleep state as the sleep state only because the motion score (i.e., motion intensity and motion frequency) is equal to 0 or a small value. Therefore, in order to accurately determine the sleep state, the sleep quality information may be initialized (i.e., REM sleep state time=0, NREM sleep state time=0, motion time=0, non-motion time=0), and the biometric information based sleep state determination according to FIG. 12A may be started (S228).

Summarizing the steps according to FIGS. 11A to 11C, in an embodiment of the present disclosure, the motion score may be calculated based on the motion intensity and motion frequency during the predetermined sleep state check time (S219), and the primary sleep state may be determined. Then, the sleep state and/or the sleep quality may be determined using the biometric information according to steps of FIGS. 12A to 12C (i.e., determination of a secondary sleep state).

Referring to FIGS. 12A to 12C, biometric signals may be sensed (measured) by using a wearable device (e.g., wristwatch type, wristband type, or hairband type) (S229), and a heart rate may be derived using the sensed biometric signals (S230). After performing the steps S229 to S230, the heartbeat variability in the frequency domain may be derived (S231), and the derived heartbeat variability may be analyzed (S232).

When the primary sleep state is the non-sleep state and the heart rate variability (i.e., the heart rate variability value extracted during sleep) is equal to a normal heart rate variability (i.e., the heart rate variability value extracted during daily living) (S233), the secondary sleep state may be finally determined as the non-sleep state (S234), the motion and non-sleep state time during a period from the start of sleep to the awake may be calculated (S235), and the non-sleep state time may be recorded (S236).

After performing the step S236, the sleep state time may be initialized to 0, and the motion frequency may be initialized to 0 (S237). The sleep state time count may be started (S238). Then, returning to the step S205 or S206 in FIG. 11, the sleep state and sleep quality analysis (the steps S201 to S259) may be repeatedly performed until the sleeping is completed.

According to the result of the step S232, when the primary sleep state is the non-sleep state and the heart rate variability (i.e., the heart rate variability value extracted during sleep)

is greater than the normal heart rate variability (i.e., the heart rate variability value extracted during daily living) (S239), the secondary sleep state may be finally determined as the REM sleep state (S240), the non-motion time during the period from the start of sleep to the awake may be calculated (S241), the REM sleep state time may be calculated (S242), and the REM sleep state time may be recorded (S243).

After performing the steps S239 to S243, returning to the step S229, the sleep state and sleep quality analysis may be repeatedly performed until the sleeping is completed.

According to the result of the step S232, when the primary sleep state is the sleep state and the heart rate variability (i.e., the heart rate variability value extracted during sleep) is greater than the normal heart rate variability (i.e., the heart rate variability value extracted during daily living) (S244), the secondary sleep state may be finally determined as the REM sleep state (S245), the non-motion time during the period from the start of sleep to the awake may be calculated (S246), the REM sleep state time may be calculated (S247), and the REM sleep state time may be recorded (S248).

After performing the steps S244 to S248, returning to the step S229, the sleep state and sleep quality analysis may be repeatedly performed until the sleeping is completed.

According to the result of the step S232, if the primary sleep state is the sleep state and the heart rate variability (i.e., the heart rate variability value extracted during sleep) is smaller than the normal heart rate variability (i.e., the heart rate variability value extracted during daily living) (S244), the secondary sleep state may be finally determined as the NREM sleep state, the subdivided NREM sleep state (S1, S2, S3 or S4) may be determined using the motion score and the heart rate variability extracted during sleep based on leveling according to respective subdivided thresholds (S250), the motion time during the period from the start of sleep to the awake may be calculated (S251), the NREM sleep state time may be calculated (S252), and the NREM sleep state time may be recorded (S253).

After performing the steps S249 to S255, returning to the step S229, the sleep state and sleep quality analysis may be repeatedly performed until the sleeping is completed.

According to the result of the step S232, when the primary sleep state is the sleep state and the heart rate variability (i.e., the heart rate variability value extracted during sleep) is equal to the normal heart rate variability (i.e., the heart rate variability value extracted during daily living) (S254), the secondary sleep state may be finally determined as the non-sleep state (S255), the motion and non-sleep state time during the period from the start of sleep to the awake may be calculated (S256), and the non-sleep state time may be recorded (S257).

After performing the steps S254 to S257, the sleep state time may be initialized to 0 and the motion frequency may be initialized to 0 (S258), and the sleep state time count may be started (S259). Then, returning to the step S205 or S2076, and the sleep state and sleep quality analysis may be repeatedly performed until the sleeping is completed.

The embodiments of the present disclosure may be implemented as program instructions executable by a variety of computers and recorded on a computer readable medium. The computer readable medium may include a program instruction, a data file, a data structure, or a combination thereof. The program instructions recorded on the computer readable medium may be designed and configured specifically for the present disclosure or can be publicly known and available to those who are skilled in the field of computer software.

Examples of the computer readable medium may include a hardware device such as ROM, RAM, and flash memory, which are specifically configured to store and execute the program instructions. Examples of the program instructions include machine codes made by, for example, a compiler, as well as high-level language codes executable by a computer, using an interpreter. The above exemplary hardware device can be configured to operate as at least one software module in order to perform the embodiments of the present disclosure, and vice versa.

While the embodiments of the present disclosure and their advantages have been described in detail, it should be understood that various changes, substitutions and alterations may be made herein without departing from the scope of the present disclosure.

What is claimed is:

1. A sleep state determination method using biometric and motion information, the sleep state determination method comprising:
   acquiring motion information of a user using a motion sensor; determining a primary sleep state of the user based on the acquired motion information;
   acquiring biometric information of the user using a biometric sensor after the primary sleep state is determined; and
   determining a final sleep state of the user by combining the acquired biometric information and the primary sleep state,
   wherein the biometric information includes a photoplethysmography (PPG) signal of the user,
   wherein the determining a final sleep state comprises:
   calculating peak-to-valley values of the PPG signal;
   deriving a graph of which a horizontal axis represents the time and a vertical axis represents the peak-to-valley values of the PPG signal; and
   calculating a heart rate variability by analyzing a frequency in the graph;
   comparing the calculated heart rate variability with a predetermined normal heart rate variability,
   wherein the predetermined normal heart rate variability is collected in advance and is a heart rate variability calculated at least once a day; and
   determining the final sleep state by combining a result of the comparison and the primary sleep state.

2. The sleep state determination method according to claim 1, wherein the determining a primary sleep state comprises:
   calculating a motion intensity and a motion frequency from the motion information;
   calculating a motion score based on the calculated motion intensity and motion frequency; and
   determining the primary sleep state of the user based on the calculated motion score.

3. The sleep state determination method according to claim 2, wherein the motion frequency is a number of times the motion intensity exceeds a preset threshold during a predetermined time.

4. The sleep state determination method according to claim 2, wherein, in the determining the primary sleep state of the user based on the calculated motion score, the primary sleep state of the user is determined to be one of a sleep state or a non-sleep state based on the motion score.

5. The sleep state determination method according to claim 1, wherein, in the determining the final sleep state, when the calculated heart rate variability is greater than the predetermined normal heart rate variability, the final sleep state is determined to be a Rapid Eye Movement (REM) sleep state regardless of the primary sleep state.

6. The sleep state determination method according to claim 1, wherein, in the determining the final sleep state, when the calculated heart rate variability is smaller than the predetermined normal heart rate variability and the primary sleep state is a sleep state, the final sleep state is determined to be a non-REM (NREM) sleep state.

7. A sleep state determination apparatus using biometric and motion information, the apparatus comprising at least one processor and a memory storing at least one instruction executed by the at least one processor, wherein the at least one instruction is configured to:
    acquire motion information of a user using a motion sensor;
    determine a primary sleep state of the user based on the acquired motion information;
    acquire biometric information of the user using a biometric sensor after the primary sleep state is determined; and
    determine a final sleep state of the user by combining the acquired biometric information and the primary sleep state,
    wherein the biometric information includes a photoplethysmography (PPG) signal of the user,
    wherein, in the determining of the final sleep state, the at least one instruction is further configured to:
    calculate peak-to-valley values of the PPG signal;
    derive a graph of which a horizontal axis represents the time and a vertical axis represents the peak-to-valley values of the PPG signal; and
    calculate a heart rate variability by analyzing a frequency in the graph;
    compare the calculated heart rate variability with a predetermined normal heart rate variability,
    wherein the predetermined normal heart rate variability is collected in advance and is a heart rate variability calculated at least once a day; and
    determine the final sleep state by combining a result of the comparison and the primary sleep state.

8. The sleep state determination apparatus according to claim 7, wherein, in the determining of the primary sleep state, the at least one instruction is further configured to:
    calculate a motion intensity and a motion frequency from the motion information;
    calculate a motion score based on the calculated motion intensity and motion frequency; and
    determine the primary sleep state of the user based on the calculated motion score.

9. The sleep state determination apparatus according to claim 8, wherein the motion frequency is a number of times the motion intensity exceeds a preset threshold during a predetermined time.

10. The sleep state determination apparatus according to claim 8, wherein, in the determining of the primary sleep state, the at least one instruction is further configured to determine the primary sleep state of the user to be one of a sleep state or a non-sleep state based on the motion score.

11. The sleep state determination apparatus according to claim 7, wherein, in the determining of the final sleep state, the at least one instruction is further configured to determine the final sleep state to be a Rapid Eye Movement (REM) sleep state regardless of the primary sleep state when the calculated heart rate variability is greater than the predetermined normal heart rate variability.

12. The sleep state determination apparatus according to claim 7, wherein, in the determining of the final sleep state, the at least one instruction is further configured to determine the final sleep state to be a non-sleep regardless of the primary sleep state when the calculated heart rate variability is equal to the predetermined normal heart rate variability within a predetermined error range.

13. The sleep state determination apparatus according to claim 7, wherein, in the determining of the final sleep state, the at least one instruction is further configured to determine the final sleep state to be a non-REM (NREM) sleep state when the calculated heart rate variability is smaller than the predetermined normal heart rate variability and the primary sleep state is a sleep state.

* * * * *